United States Patent
Tobey et al.

(10) Patent No.: US 12,127,781 B2
(45) Date of Patent: Oct. 29, 2024

(54) VESSEL SEALING INSTRUMENT WITH SEAL PLATES FOR DIRECTING THE FLOW OF ENERGY

(71) Applicant: Covidien LP, Mansfield, MA (US)

(72) Inventors: Samuel W. Tobey, Erie, CO (US); James D. Allen, IV, Broomfield, CO (US); Kenlyn S. Bonn, Lakewood, CO (US); Jennifer R. Mchenry, Denver, CO (US); William E. Robinson, Erie, CO (US)

(73) Assignee: Covidien LP, Mansfield, MA (US)

( * ) Notice: Subject to any disclaimer, the term of this patent is extended or adjusted under 35 U.S.C. 154(b) by 456 days.

(21) Appl. No.: 16/917,585

(22) Filed: Jun. 30, 2020

(65) Prior Publication Data

US 2021/0401485 A1  Dec. 30, 2021

(51) Int. Cl.
*A61B 18/14* (2006.01)
*A61B 18/00* (2006.01)
*A61B 18/12* (2006.01)

(52) U.S. Cl.
CPC ...... *A61B 18/1442* (2013.01); *A61B 18/1445* (2013.01); *A61B 2018/00083* (2013.01); *A61B 2018/00428* (2013.01); *A61B 2018/0063* (2013.01); *A61B 2018/126* (2013.01)

(58) Field of Classification Search
CPC ............ A61B 18/1442; A61B 18/1445; A61B 2018/00083; A61B 2018/00428; A61B 2018/0063; A61B 2018/126
USPC .............................. 606/51–52, 169, 205–207
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 5,151,102 A | 9/1992 | Kamiyama et al. |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,403,312 A | 4/1995 | Yates et al. |
| D358,887 S | 5/1995 | Feinberg |
| 5,626,578 A | 5/1997 | Tihon |
| 5,658,281 A | 8/1997 | Heard |
| D384,413 S | 9/1997 | Zlock et al. |
| 5,688,270 A | 11/1997 | Yates et al. |
| 5,766,166 A | 6/1998 | Hooven |
| H1745 H | 8/1998 | Paraschac |
| 5,810,811 A | 9/1998 | Yates et al. |
| 5,833,690 A | 11/1998 | Yates et al. |

(Continued)

OTHER PUBLICATIONS

Extended European Search Report for application No. 21182941 dated Nov. 18, 2021.

*Primary Examiner* — Khadijeh A Vahdat

(57) ABSTRACT

Jaw members of end effector assemblies include sealing plates configured to direct the amount and flow of energy through the sealing plates. The sealing plates may have a height varying from a minimal height to a maximum height along a width or a length of the sealing plate and/or a sealing surface including at least two impedance zones having different impedance values.

16 Claims, 10 Drawing Sheets

(56) References Cited

U.S. PATENT DOCUMENTS

| | | |
|---|---|---|
| D402,028 S | 12/1998 | Grimm et al. |
| 5,876,401 A | 3/1999 | Schulze et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| 6,066,137 A | 5/2000 | Greep |
| 6,086,586 A | 7/2000 | Hooven |
| H1904 H | 10/2000 | Yates et al. |
| 6,162,220 A | 12/2000 | Nezhat |
| D449,886 S | 10/2001 | Tetzlaff et al. |
| 6,334,860 B1 | 1/2002 | Dorn |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,458,128 B1 | 10/2002 | Schulze |
| D465,281 S | 11/2002 | Lang |
| D466,209 S | 11/2002 | Bon |
| 6,656,177 B2 | 12/2003 | Truckai et al. |
| D493,888 S | 8/2004 | Reschke |
| 6,770,072 B1 | 8/2004 | Truckai et al. |
| 6,773,409 B2 | 8/2004 | Truckai et al. |
| D496,997 S | 10/2004 | Dycus et al. |
| D499,181 S | 11/2004 | Dycus et al. |
| D502,994 S | 3/2005 | Blake, III |
| 6,926,716 B2 | 8/2005 | Baker et al. |
| D509,297 S | 9/2005 | Wells |
| 6,953,461 B2 | 10/2005 | McClurken et al. |
| 7,025,763 B2 | 4/2006 | Karasawa et al. |
| D525,361 S | 7/2006 | Hushka |
| D531,311 S | 10/2006 | Guerra et al. |
| 7,135,020 B2 | 11/2006 | Awes et al. |
| D533,274 S | 12/2006 | Visconti et al. |
| D533,942 S | 12/2006 | Kerr et al. |
| 7,147,637 B2 | 12/2006 | Goble |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| 7,278,992 B2 | 10/2007 | Cropper et al. |
| 7,329,257 B2 | 2/2008 | Kanehira et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,419,490 B2 | 9/2008 | Falkenstein et al. |
| D582,038 S | 12/2008 | Swoyer et al. |
| 7,597,693 B2 | 10/2009 | Garrison |
| 7,632,269 B2 | 12/2009 | Truckai et al. |
| 7,686,804 B2 | 3/2010 | Johnson et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,799,026 B2 | 9/2010 | Schechter et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| 8,388,646 B2 | 3/2013 | Chojin |
| D680,220 S | 4/2013 | Rachlin |
| 8,469,956 B2 | 6/2013 | McKenna et al. |
| 8,597,297 B2 | 12/2013 | Couture et al. |
| 8,734,445 B2 | 5/2014 | Johnson et al. |
| 8,784,417 B2 | 7/2014 | Hanna |
| 10,278,768 B2 | 5/2019 | Keller et al. |
| 2002/0099368 A1 | 7/2002 | Schulze |
| 2002/0107517 A1 | 8/2002 | Witt et al. |
| 2002/0111624 A1 | 8/2002 | Witt et al. |
| 2004/0082952 A1 | 4/2004 | Dycus et al. |
| 2006/0271038 A1 | 11/2006 | Johnson et al. |
| 2009/0182322 A1 | 7/2009 | D'Amelio |
| 2009/0216229 A1 | 8/2009 | Chojin |
| 2010/0016857 A1 | 1/2010 | McKenna et al. |
| 2010/0145335 A1 | 6/2010 | Johnson et al. |
| 2010/0179543 A1 | 7/2010 | Johnson et al. |
| 2012/0059374 A1 | 3/2012 | Johnson et al. |
| 2013/0079764 A1 | 3/2013 | Schaller et al. |
| 2013/0185922 A1 | 7/2013 | Twomey et al. |
| 2013/0255063 A1 | 10/2013 | Hart et al. |
| 2014/0353869 A1 | 12/2014 | Goodman et al. |
| 2015/0282867 A1* | 10/2015 | Keller ............... A61B 18/1445 606/52 |
| 2016/0038224 A1 | 2/2016 | Couture et al. |
| 2016/0074095 A1 | 3/2016 | Strobl et al. |
| 2016/0175025 A1 | 6/2016 | Strobl |
| 2019/0142504 A1 | 5/2019 | Tsuruta |
| 2019/0209233 A1 | 7/2019 | Orton |

\* cited by examiner

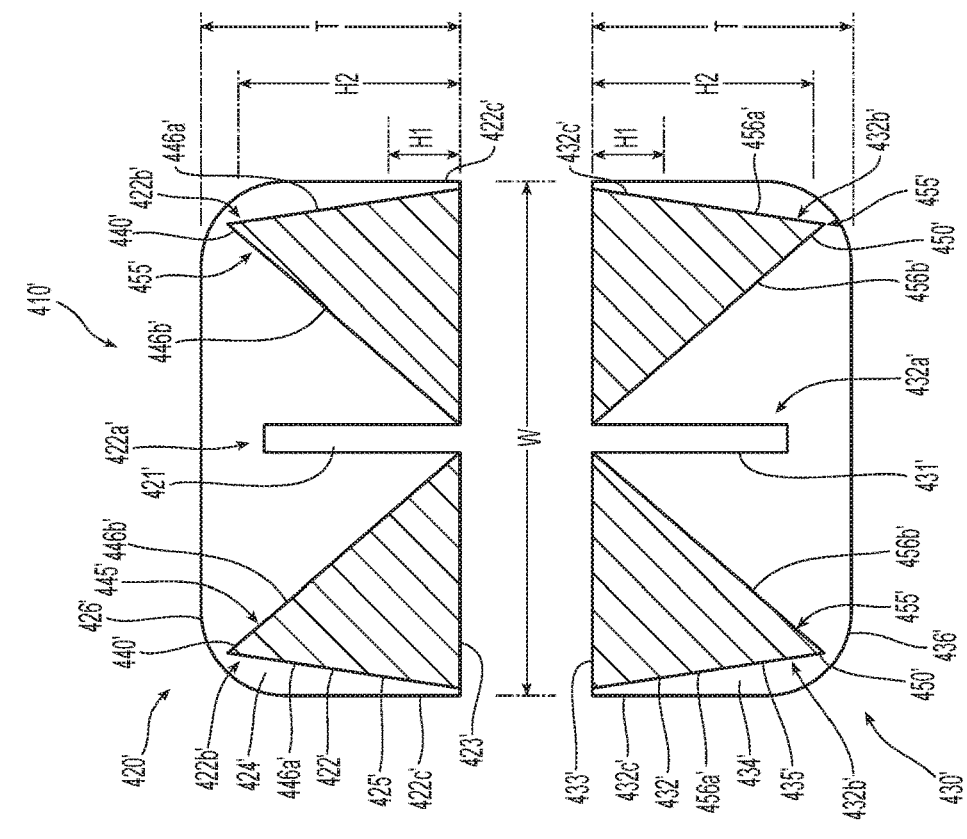
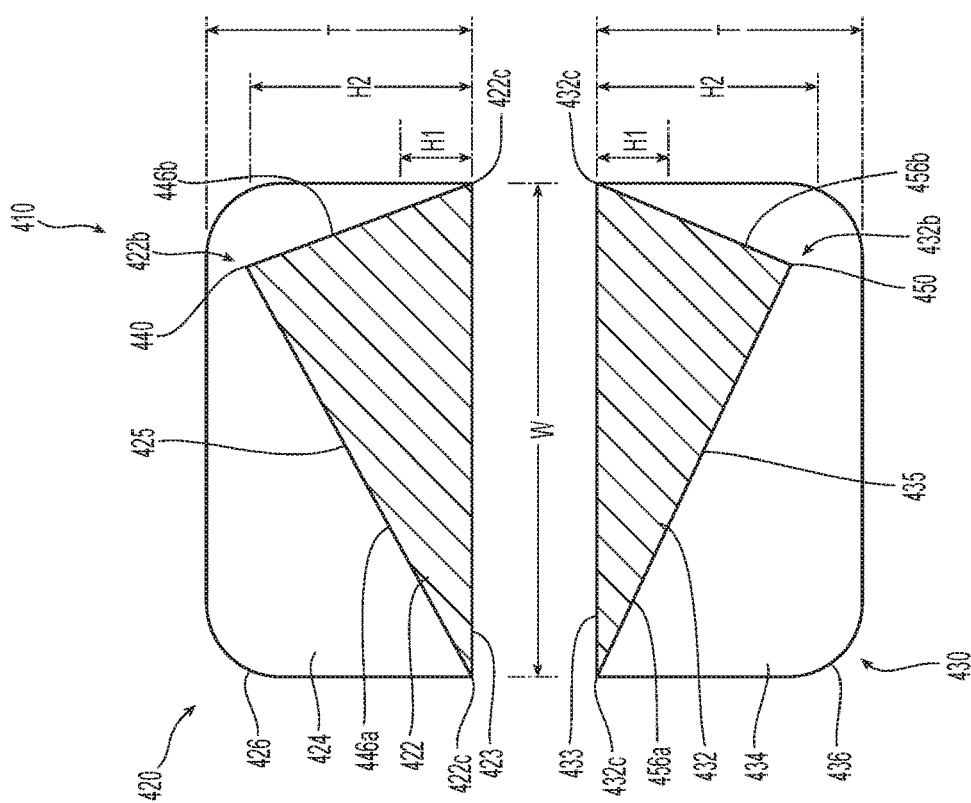
Fig. 4B
Fig. 4A

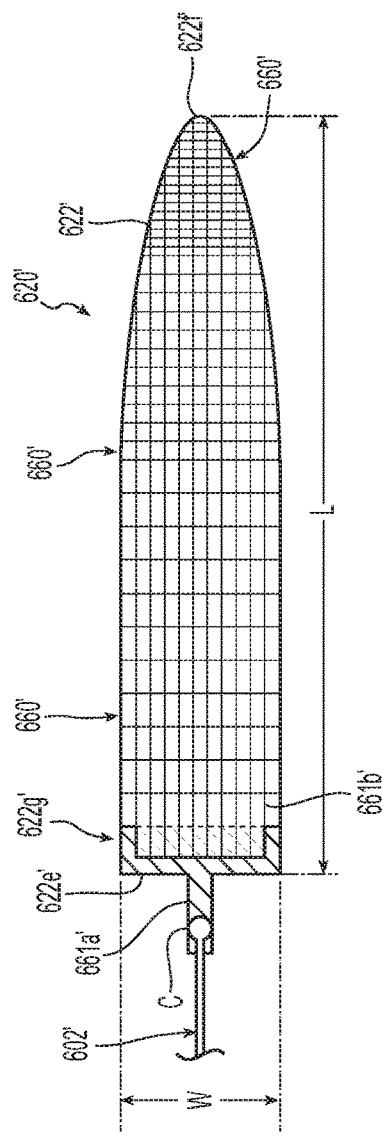
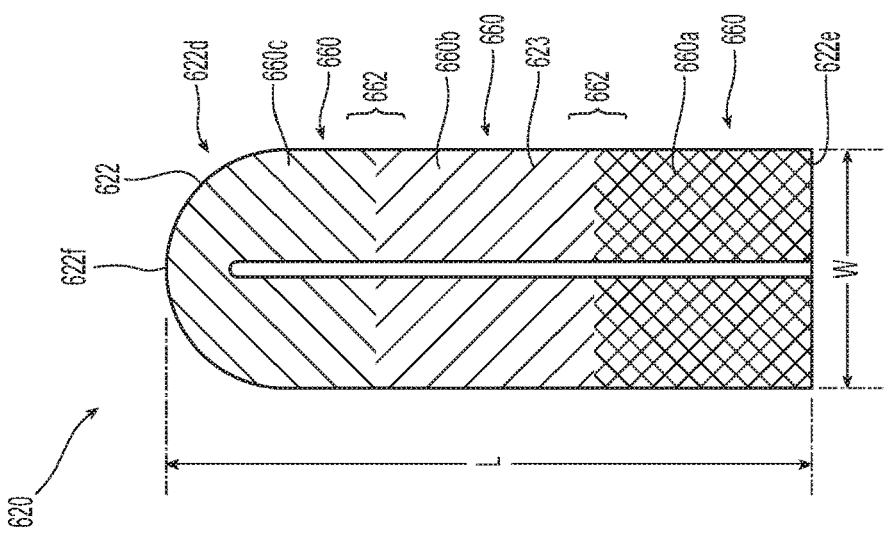
Fig. 6B
Fig. 6A

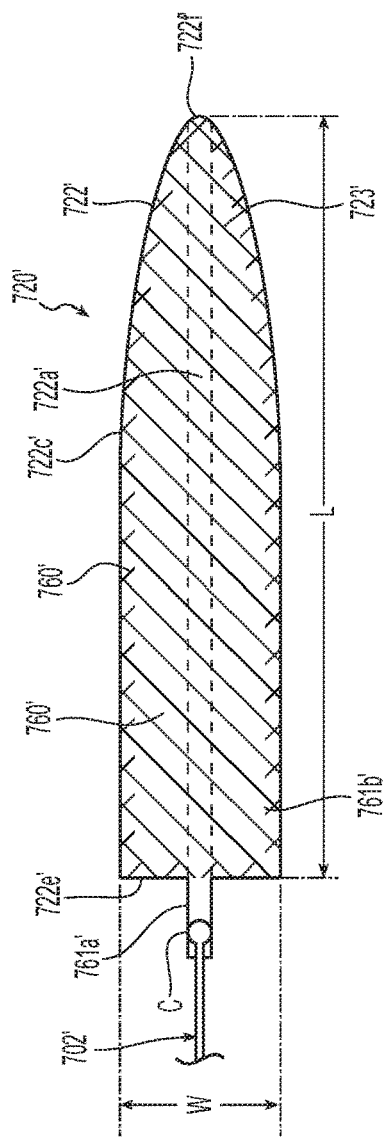
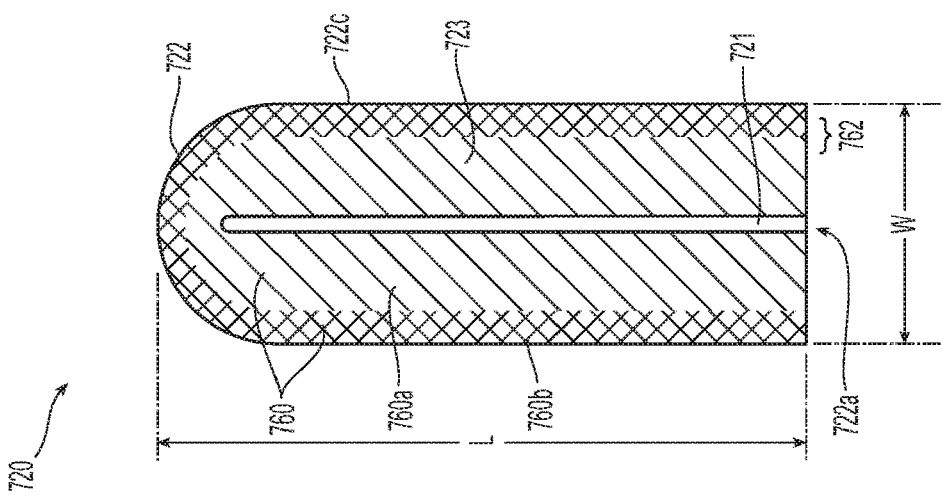
Fig. 7B
Fig. 7A

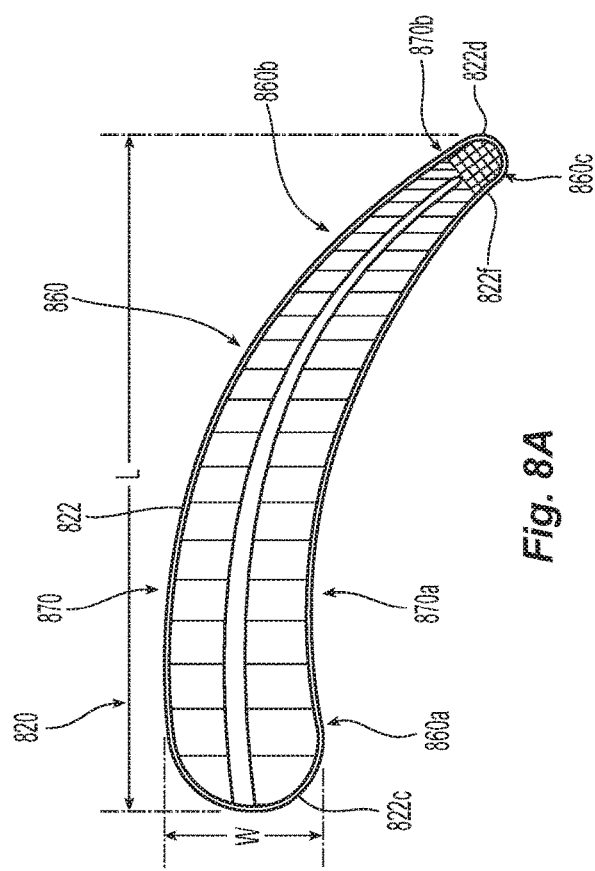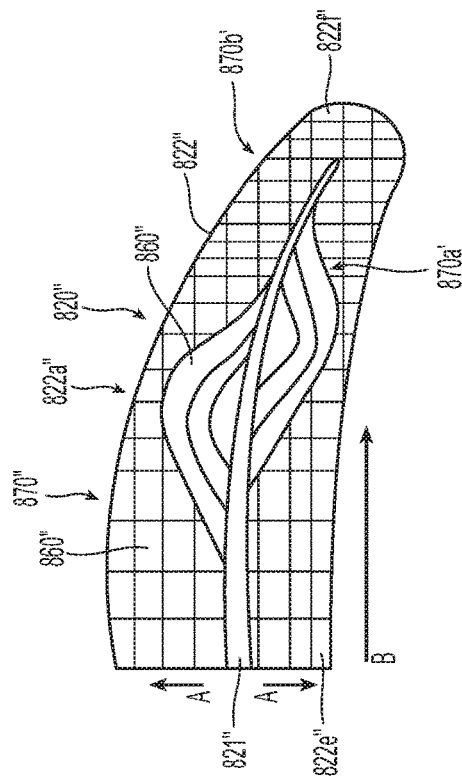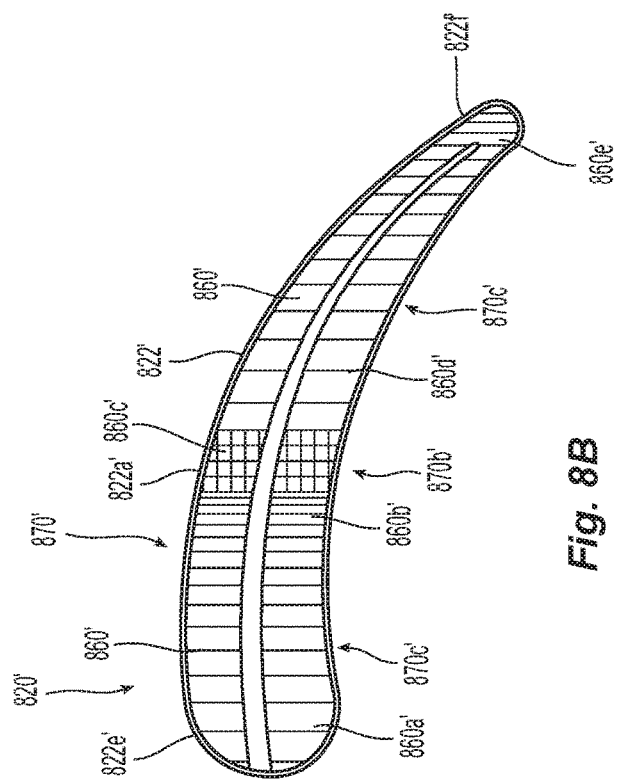

VESSEL SEALING INSTRUMENT WITH SEAL PLATES FOR DIRECTING THE FLOW OF ENERGY

FIELD

The present technology is generally related an apparatus for performing an electrosurgical procedure. More particularly, the present technology relates to a vessel sealing instrument that employs an end effector assembly including sealing plates that direct the flow of energy to enhance sealing and severing of tissue.

BACKGROUND

Electrosurgical apparatuses (e.g., electrosurgical forceps) are well known in the medical arts and typically include a handle, a shaft, and an end effector assembly operatively coupled to a distal end of the shaft that is configured to manipulate tissue (e.g., grasp and seal tissue). Electrosurgical forceps utilize both mechanical clamping action and electrical energy to effect homeostasis by heating the tissue and blood vessels to coagulate, cauterize, fuse, seal, cut, desiccate, and/or fulgurate tissue.

Electrosurgical forceps may be open forceps for use when accessing open body cavities or open surgical access points, e.g., incisions, or endoscopic forceps for remotely accessing organs through smaller, puncture-like incisions. With endoscopic surgeries, patients tend to benefit from less scarring, less pain, and reduced healing time. The endoscopic forceps is inserted into the patient through one or more various types of cannulas or access ports (typically having an opening that ranges from about five millimeters to about fifteen millimeters) that has been made with a trocar.

Open and endoscopic forceps both utilize an end effector assembly disposed at a distal end thereof for treating tissue between a pair of opposing jaw members. Each jaw member includes an electrically conductive surface or sealing plate used to treat or seal tissue grasped therebetween.

SUMMARY

This disclosure generally relates to directing the flow of energy (e.g., bipolar energy) in an end effector assembly. Sealing plates of the end effector assembly are of variable thickness and/or incorporate conductive, semiconductive, or insulative materials on the sealing plates to direct the amount and flow of energy through the sealing plates and thus, through tissue thereby increasing seal reliability and/or biasing or decreasing thermal spread. The techniques of this disclosure may be utilized to improve sealing of tissue in cases of non-parallel closure of the end effector assembly when the tissue being treated is not centered between jaw members of the end effector assembly.

In one aspect, the disclosure provides a jaw member including a sealing plate and an insulator supporting the sealing plate thereon. The sealing plate has a length, a width, and a height. The height varies from a minimal height to a maximum height along the width or the length of the sealing plate.

The height of the sealing plate may vary across the width of the sealing plate and be consistent along the length of the sealing plate. The sealing plate may include a sealing surface and an outwardly facing surface tapering to an apex, and the maximum height of the sealing plate may extend from the sealing surface to the apex. The outwardly facing surface may include legs extending from outer edges of the sealing plate to the apex. The legs may be equal in length such that the apex is disposed in a central portion of the sealing plate, or the legs may have different lengths such that the apex is disposed in a side portion of the sealing plate.

The height of the sealing plate may vary along the length of the sealing plate and be consistent across the width of the sealing plate. The sealing plate may include a sealing surface and an outwardly facing surface tapering to an apex, and the maximum height of the sealing plate may extend from the sealing surface to the apex. The outwardly facing surface may include legs extending from proximal and distal ends of the sealing plate to the apex. The apex may be disposed in a tip portion of the sealing plate. The minimal height of the sealing plate may be defined in a heel portion of the sealing plate.

In another aspect, the disclosure provides a jaw member including a sealing plate and an insulator supporting the sealing plate thereon. The sealing plate includes a sealing surface having at least two impedance zones. The at least two impedance zones includes a first zone having a first impedance value and a second zone having a second impedance value that is different from the first impedance value.

The sealing surface may further include an interphase disposed between the first and second zones. The interphase may have an impedance value that gradually transitions from the first zone to the second zone.

Each of the at least two impedance zones may be homogeneous.

The first and second zones may be positioned longitudinally adjacent to each other. The sealing plate may further include a third zone having a third impedance value that is different from the first and second impedance values. The first zone may be disposed on a proximal portion of the sealing surface, the second zone may be disposed on an intermediate portion of the sealing surface, and the third zone may be disposed on a distal portion of the sealing surface. The third impedance value may be less than the second impedance value which may be less than the first impedance value.

The first and second zones may be concentric with each other. The first zone may be disposed inside of the second zone, and the first impedance value may be less than the second impedance value.

The at least two impedance zones may be coatings of conductive materials disposed on the sealing surface of the sealing plate.

In yet another aspect, the disclosure provides a jaw member including a support base, an insulator supported within the support base, and a sealing plate supported on the insulator. The sealing plate has a length, a width, and a height. The height varies from a minimal height to a maximum height along the width of the sealing plate.

The sealing plate may include a sealing surface and an outwardly facing surface positioned adjacent to the insulator. The outwardly facing surface may have at least one apex, and the maximum height of the sealing plate may extend from the sealing surface to the at least one apex.

The sealing plate may include two apexes. The outwardly facing surface of the sealing plate may include two sets of legs with each set of the two sets of legs extending to one of the two apexes. A first leg of each of the two sets of legs may extend from an outer edge of the sealing plate to the respective apex, and a second leg of each of the two sets of legs may extend from a central portion of the sealing plate to the respective apex. The first and second legs may have different lengths. At least one of the first or second legs may be non-linear.

A tissue contacting surface of the jaw member may define a length and width, and the width of the sealing plate may be less than the width of the jaw member. The tissue contacting surface may be nonplanar. The sealing plate may be offset in a height direction relative to the insulator.

In another aspect, the disclosure provides a jaw member including a support base, an insulator supported within the support base, and a sealing plate supported on the insulator. The sealing plate includes a sealing surface having at least two impedance zones. The at least two impedance zones have different impedance values.

The at least two impedance zones may be positioned longitudinally adjacent to each other. The at least two impedance zones may be concentric with each other. The at least two impedance zones may be formed from a material having a different thickness in each of the at least two impedance zones.

The sealing plate may include a first conductive material disposed at a proximal end of the sealing plate, and a second conductive material positioned over at least a portion of the first material and extending distally therefrom across the sealing surface to a distal end of the sealing plate. The first conductive material may have a resistivity lower than that of the second conductive material.

The sealing plate may include a first impedance region including the at least two impedance zones and a second impedance region including at least one impedance zone. The first impedance region may extend from a proximal end of the sealing plate towards a distal end of the sealing plate adjacent to a tip portion, and the second impedance region may be disposed at the tip portion of the sealing plate. The first impedance region may extend from a proximal end of the sealing plate to a central portion of the sealing plate, the second impedance region may be disposed about the central portion of the sealing plate, and a third impedance region may extend from the central portion to a distal end of the sealing plate. The first impedance region may be disposed within the second impedance region.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 4A is a cross-sectional view of jaw members in accordance with another embodiment of the disclosure;

FIG. 4B is a cross-sectional view of jaw members in accordance with yet another embodiment of the disclosure;

FIG. 6A is a top view of a sealing plate of a jaw member in accordance with an embodiment of the disclosure;

FIG. 6B is a top view of a sealing plate of a jaw member in accordance with another embodiment of the disclosure;

FIG. 7A is a top view of a sealing plate of a jaw member in accordance with yet another embodiment of the disclosure;

FIG. 7B is a top view of a sealing plate of a jaw member in accordance with another embodiment of the disclosure; and FIGS. 8A-8C are top views of sealing plates of jaw members in accordance with embodiments of the disclosure.

DETAILED DESCRIPTION

Figure 1:
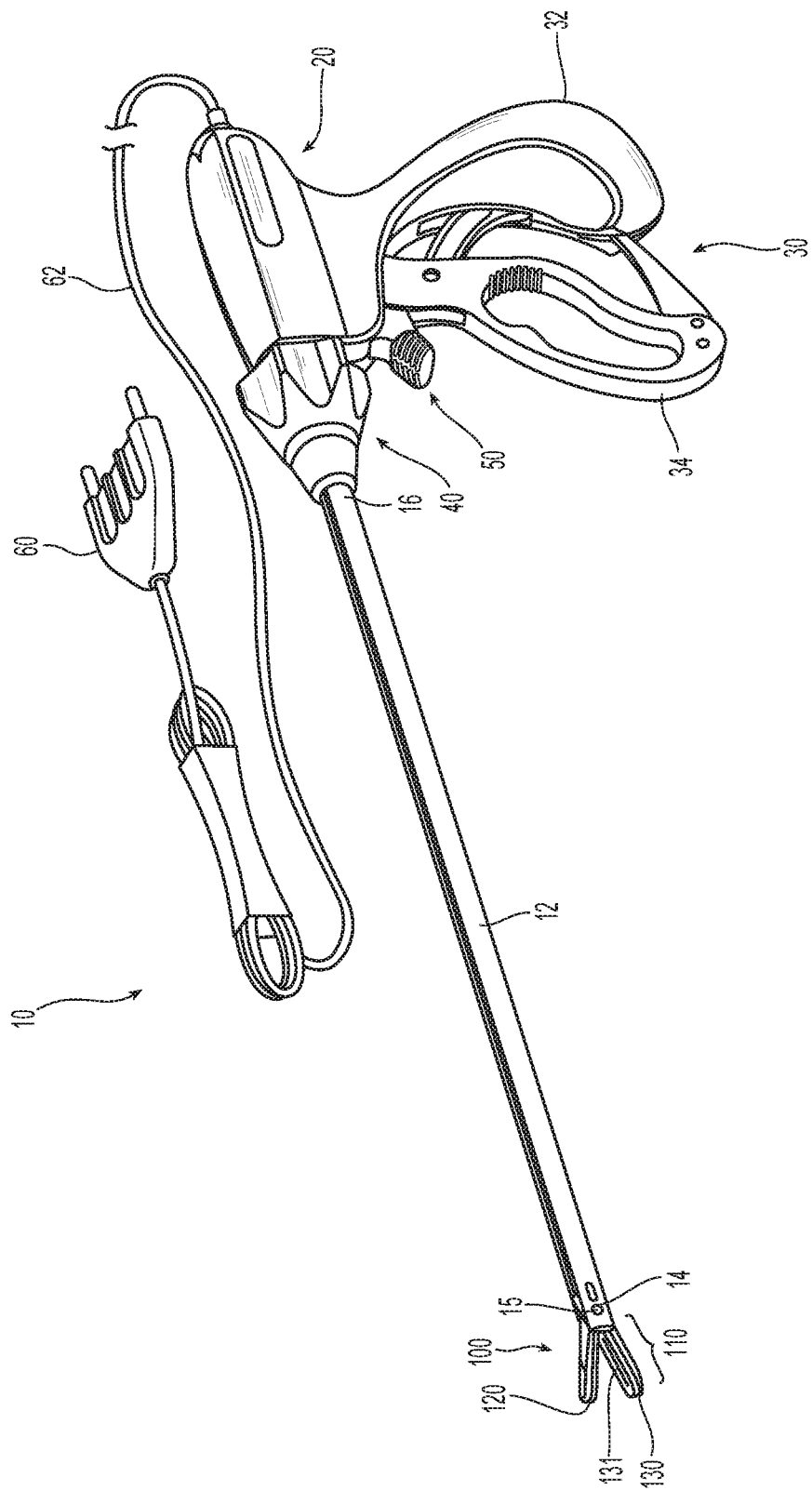
FIG. 1 is a perspective view of an endoscopic bipolar forceps in accordance with an embodiment of the disclosure.

Embodiments of the disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals may refer to similar or identical elements throughout the description of the figures. It should be understood that various components of the disclosure, such as those numbered in the 100 series, correspond to components of the disclosure similarly numbered in each of the 200 series, 300 series, 400 series, and so on such that redundant explanation of similar components of embodiments need not be repeated herein. As shown in the drawings and described throughout the following description, as is traditional when referring to relative positioning of a surgical instrument, the term "proximal" refers to a portion (e.g., an end) of the apparatus which is closer to the user and the term "distal" refers to a portion of the apparatus which is farther away from the user. The term "clinician" refers to any medical professional (e.g., doctor, surgeon, nurse, or the like) performing a medical procedure involving the use of embodiments described herein.

Turning now to FIG. 1, an instrument generally identified as endoscopic bipolar forceps 10 may be used during various surgical procedures and includes a housing 20, a handle assembly 30, a rotating assembly 40, a trigger assembly 50, and an end effector assembly 100 that mutually cooperate to grasp, seal, and divide tubular vessels and vascular tissues. The forceps 10 includes a shaft 12 that has a distal end 14 dimensioned to mechanically engage the end effector assembly 100 and a proximal end 16 that mechanically engages the housing 20. The proximal end 16 of the shaft 12 mechanically engages the rotating assembly 40 to facilitate rotation of a jaw assembly 110 of the end effector assembly 100.

The handle assembly 30 includes a fixed handle 32 and a movable handle 34. The fixed handle 32 is integrally associated with the housing 20 and the movable handle 34 is movable relative to the fixed handle 32 to actuate a pair of opposing jaw members 120, 130 of the jaw assembly 110. The movable handle 34 imparts movement of the jaw members 120, 130 about a pivot pin 15 from an open position wherein the jaw members 120, 130 are disposed in spaced relation relative to one another for approximating tissue, to a clamping or closed position wherein the jaw members 120, 130 cooperate to grasp tissue therebetween (e.g., for sealing and/or dividing purposes).

The trigger assembly 50 is selectively movable by a clinician to energize the jaw assembly 110. The movable handle 34 and the trigger assembly 50 are typically of unitary construction and are operatively connected to the housing 20 and the fixed handle 32 during the assembly process. The forceps 10 also includes an electrical interface or plug 60 which connects the forceps 10 to a source of electrosurgical energy, e.g., an electrosurgical generator (not shown). An electrical cable 62 extends from the plug 60 and is securely connected to the forceps 10. The cable 62 is internally divided within the housing 20 to transmit electrosurgical energy through various electrical feed paths to the jaw assembly 110.

The forceps 10 may be designed such that it is fully or partially disposable depending upon a particular purpose or to achieve a particular result. For example, the jaw assembly 110 may be selectively and releasably engageable with the distal end 14 of the shaft 12 and/or the proximal end 16 of the shaft 12 may be selectively and releasably engageable with the housing 20 and the handle assembly 30. In either of these two instances, the forceps 10 would be considered "partially disposable" or "reposable", e.g., a new or different jaw assembly 110 (or jaw assembly 110 and shaft 12) selectively replaces the old jaw assembly 110, as needed.

Examples of forceps are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 (now U.S. Pat. No. 7,156,846) entitled "VESSEL SEALER AND DIVIDER FOR USE WITH SMALL TROCARS AND CANNULAS", the entire contents of each of which are hereby incorporated by reference herein.

Figure 2:
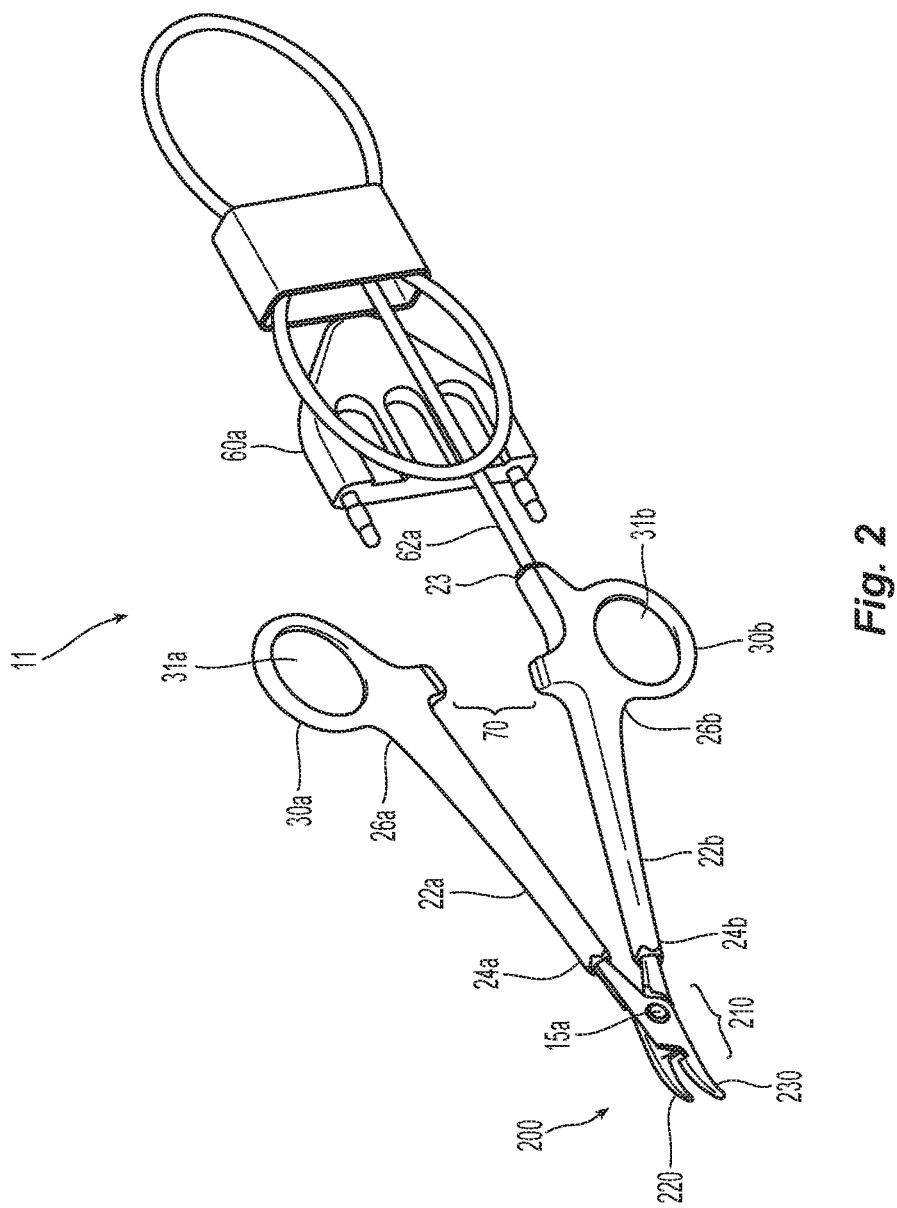
FIG. 2 is a perspective view of an open bipolar forceps in accordance with an embodiment of the disclosure.

With regard to FIG. 2, an open bipolar forceps 11 for use with various surgical procedures is shown. The forceps 11 includes a pair of opposing shafts 22a and 22b having an end effector assembly 200 attached to distal ends 24a and 24b thereof, respectively. The end effector assembly 200 is similar in design to the end effector assembly 100 and includes a jaw assembly 210 having a pair of opposing jaw members 220, 230 that are pivotably connected about a pivot pin 15a and that are movable relative to one another to grasp tissue.

Each shaft 22a, 22b includes a handle 30a, 30b, respectively, disposed at the proximal end 26a, 26b thereof. Each handle 30a, 30b defines a finger hole 31a, 31b, respectively, therethrough for receiving a finger of a clinician. The finger holes 31a, 31b facilitate movement of the shafts 22a, 22b relative to one another which, in turn, pivot the jaw members 220, 230 from an open position wherein the jaw members 220, 230 are disposed in spaced relation relative to one another, to a clamping or closed position wherein the jaw members 220, 230 cooperate to grasp tissue therebetween.

One of the shafts 22a, 22b includes a proximal shaft connector or flange 23 which is designed to connect the forceps 11 to a source of electrosurgical energy, such as an electrosurgical generator (not shown). The flange 23 mechanically secures an electrosurgical cable 62a to the forceps 11 such that a clinician may selectively apply electrosurgical energy as needed. The cable 62a includes a plug 60a, similar to plug 60 of FIG. 1. A ratchet 70 is included for selectively locking the jaw members 220, 230 relative to one another at various positions during pivoting.

Examples of forceps are shown and described in commonly-owned U.S. application Ser. No. 10/474,170 (now U.S. Pat. No. 7,582,087) entitled "VESSEL SEALING INSTRUMENT" and commonly owned U.S. application Ser. No. 11/333,165 (now U.S. Pat. No. 7,909,823) entitled "OPEN VESSEL SEALING INSTRUMENT", the entire contents of each of which are hereby incorporated by reference herein.

Figure 3B:
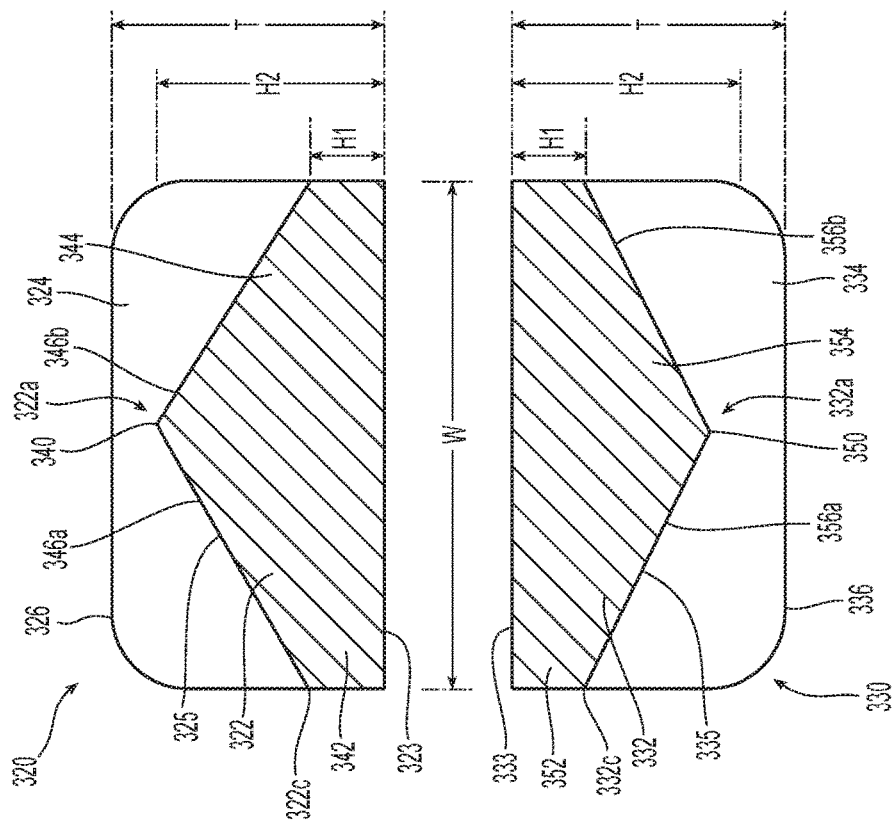
FIG. 3B is a cross-sectional view of the jaw members of FIG. 3A, taken along section line 3B-3B of FIG. 3A.
Figure 3A:
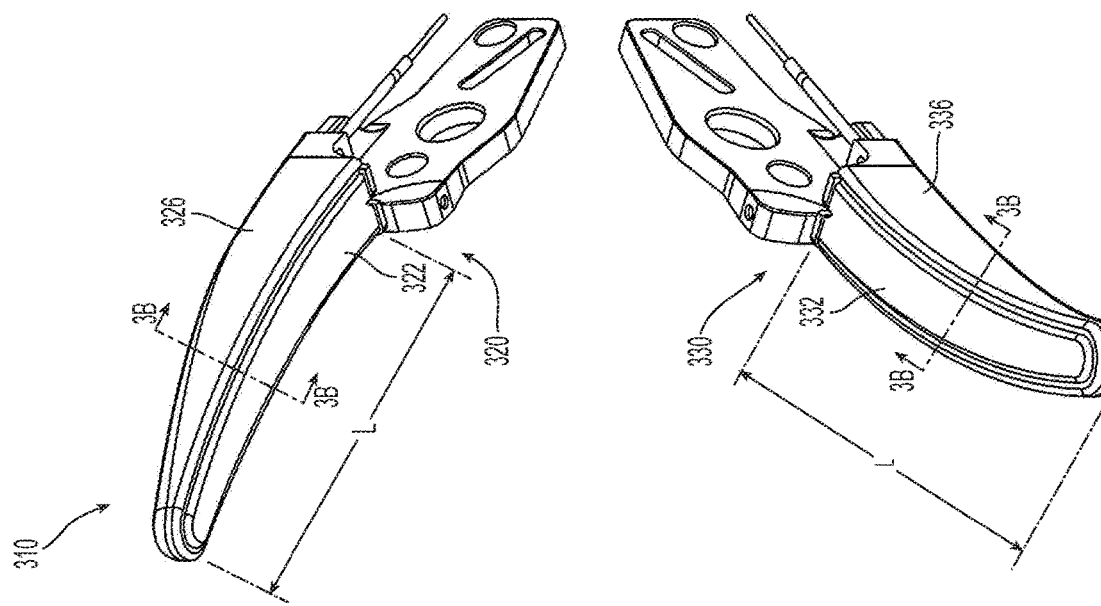
FIG. 3A is a perspective view of jaw members in accordance with an embodiment of the disclosure.

FIGS. 3A and 3B show opposing jaw members 320, 330 of a jaw assembly 310. The jaw assembly 310 is contemplated for use with the endoscopic forceps 10 of FIG. 1 or the open forceps 11 of FIG. 2. For the purposes herein, either an endoscopic instrument or an open instrument may be utilized with the end effector assembly described herein. Different electrical and/or mechanical connections and considerations apply to each particular type of instrument, as should be understood by one skilled in the art, however, the novel aspects with respect to the end effector assembly and its operating characteristics remain generally consistent with respect to both the endoscopic and open designs.

Similar to jaw members 120, 130 of FIG. 1 and jaw members 220, 230 of FIG. 2, each of the jaw members 320, 330 generally includes: electrically conductive sealing plates or substrates 322, 332, respectively; insulators 324, 334, respectively; and insulative support bases or frames 326, 336, respectively. The support bases 326, 336 are dimensioned to support insulators 324, 334 therein which, in turn, support the sealing plates 322, 332 thereon. The sealing plates 322, 332 may be affixed atop the insulators 324, 334 and the support bases 326, 336 in any manner within the purview of those skilled in the art, such as snap-fit, overmolding, stamping, ultrasonic welding, etc. It should be understood that the insulators 324, 334 are configured and dimensioned to have a geometry complementary to the sealing plates 322, 332 to support the sealing plates 322, 332 thereon, and to the support bases 326, 336 in which the insulators 324, 334 are disposed.

The jaw members 320, 330 are generally symmetrical and include similar component features which cooperate to permit facile rotation about a pivot (see e.g., pivot pin 15, 15a of FIGS. 1, 2) to effect the grasping of tissue. The jaw members 320, 330 may be straight or may be curved to facilitate manipulation of tissue and to provide better "line of sight" for accessing targeted tissues. Either or both of the sealing plates 322, 332 and, in some cases, the insulators 324, 334 may include longitudinally-oriented knife slots (see e.g., knife slot 131 of FIG. 1) defined therethrough for reciprocation of a knife blade (not shown). Either or both of the sealing plates 322, 332 may have sealing surfaces 323, 333 that are substantially planar, or the sealing surfaces 323, 333 may have other configurations or features, such as stop members (not shown) to define a gap between the jaw members 320, 330 during grasping, sealing, and/or cutting of tissue, and/or grooves, ridges, etc. (not shown) to enhance the gripping of tissue during the sealing process.

With continued reference to FIGS. 3A and 3B, each of the sealing plates 322, 332 has a longitudinally extending length "L" and a transversely extending width "W." A vertical height or thickness of each of the sealing plates 322, 332 varies from a nominal or minimal height "H1" to a maximum height "H2" across the width "W" of the sealing plate 322, 332 and is consistent or uniform along the length "L" thereof. The sealing plates 322, 332 include respective inwardly facing or sealing surfaces 323, 333 and outwardly facing surfaces 325, 335 that taper to apexes 340, 350 disposed about central portions 322a, 332a of the sealing plates 322, 332 such that the thickness of the sealing plates 322, 332 is greatest about the central portions 322a, 332a of the sealing plates 322, 332.

Each of the sealing plates 322, 332 includes a base 342, 352 having the nominal height "H1" throughout the entire length "L" and width "W" of the sealing plate 322, 332. The base 342, 352 extends from the sealing surface 323, 333 outwardly towards the insulator 324, 334 such that the height "H1" of the base 342, 352 of the sealing plate 322, 332 is uniform along the length "L" and width "W" of the base 342, 352. An extension or projection 344, 354 extends from the base 342, 352 and tapers towards the apex 340, 350 such that the thickness of the extension 344, 354 varies from the nominal height "H1" to the maximum height "H2" along the width "W" of the sealing plate 322, 332 and is consistent along the length "L" of the sealing plate 322, 332. The maximum height "H2" at the apex 340, 350 of the sealing plate 322, 332 extends a majority of the height or thickness "T" of the jaw member 320, 330 and in embodiments, the maximum height "H2" of the sealing plate 322, 332 is almost the full height "T" of the jaw member 320, 330 (e.g., about 90% to about 98% of the height "T" of the jaw member 320, 330).

The extension 344, 354 includes legs 346a, 356a and 346b, 356b that taper linearly from outer edges 322c, 332c of the sealing plate 322, 332 towards the central portion 322a, 332a of the sealing plate 322, 332. The legs 346a, 356a and 346b, 356b have equal lengths such that the apex 340, 350 is centered about the sealing plate 322, 332. The legs 346a, 356a and 346b, 356b may be linear or non-linear (e.g., curved). Energy provided to the jaw assembly 310 is concentrated in the central portions 322a, 332a of the jaw members 320, 330 (e.g., the thickest part of the sealing plate 322, 332) thereby reducing thermal spread outside of the jaw members 320, 330.

FIG. 4A shows opposing jaw members 420, 430 of a jaw assembly 410. The jaw members 420, 430 include: electrically conductive sealing plates or substrates 422, 432; insulators 424, 434; and insulative support bases 426, 436. A vertical height or thickness of each of the sealing plates 422, 432 varies from a nominal or minimal height "H1" to a maximum height "H2" across the width "W" of the sealing plate 422, 432 and is consistent or uniform along the length "L" (FIG. 3A) thereof. The sealing plates 422, 432 include inwardly facing or sealing surfaces 423, 433 and outwardly facing surfaces 425, 435 that taper to apexes 440, 450 disposed about side portions 422b, 432b of the sealing plates 422, 432 such that the thickness of the sealing plate 422, 432 is greatest about one of the side portions 422b, 432b of the sealing plates 422, 432.

The outwardly facing surface 425, 435 includes legs 446a, 456a and 446b, 456b that extend respectively from outer edges 422c, 432c of the sealing plates 422, 432 adjacent the sealing surface 423, 433 and taper towards the apexes 440, 450 such that the thickness of the sealing plate 422, 432 varies from the minimal height "H1" to the maximum height "H2". The maximum height "H2" at the apex 440, 450 of the sealing plate 422, 432 extends a majority of the height or thickness "T" of the jaw member 420, 430 and in embodiments, the maximum height "H2" of the sealing plate 422, 432 is almost the full height "T" of the jaw member 420, 430.

The legs 446a, 456a and 446b, 456b have different lengths such that the apex 440, 450 is off-center of the sealing plate 422, 432. The legs 446a, 456a and 446b, 456b may be linear or non-linear (e.g., curved). Energy provided to the jaw assembly 410 more easily flows to the side portion 422b, 432b of the jaw member 420, 430 containing the apex 440, 450 (e.g., the thickest part of the sealing plate 422, 432) thus increasing thermal spread on the side portion 422b, 432b containing the apex 440, 450, with the other side portion 422b, 432b having minimal thermal spread.

FIG. 4B shows opposing jaw members 420', 430' of a jaw assembly 410'. The jaw members 420', 430' include: electrically conductive sealing plates or substrates 422', 432'; insulators 424', 434'; and insulative support bases 426', 436'. Knife slots 421', 431' extend through each of the jaw members 420', 430' about a central portion 422a', 432a' of the sealing plates 422', 432'. A vertical height or thickness of each of the sealing plates 422', 432' varies between a nominal or minimal height "H1" and a maximum height "H2" across the width "W" of the sealing plate 422', 432' and is consistent or uniform along the length "L" (FIG. 3A) thereof. The sealing plates 422', 432' include inwardly facing or sealing surfaces 423', 433' and outwardly facing surfaces 425', 435' that taper to apexes 440', 450' disposed about each of the side portions 422b', 432b' of the sealing plates 422', 432' such that the thickness of the sealing plate 422', 432' is greatest about both of the side portions 422b', 432b' of the sealing plates 422', 432'.

The outwardly facing surface 425', 435' includes two sets 445', 455' of legs 446a', 456a' and 446b', 456b'. The first leg 446a', 456a' of each set 445', 455' extends respectively from an outer edge 422c', 432c' of the sealing plate 422', 432' adjacent the sealing surface 423', 433' to the respective apex 440', 450'. The second leg 446b', 456b' of each set 445', 455' extends respectively from the knife slot 421', 431', or in embodiments devoid of a knife slot 421', 431', from about the central portion 422a', 432a' of the sealing plate 422', 432' to the respective apex 440', 450'. The first and second legs 446a', 456a' and 446b', 456b' of each set 445', 455' tapers towards the respective apex 440', 450' such that the thickness of the sealing plate 422', 432' varies from the minimal height "H1" to the maximum height "H2". The maximum height "H2" at the apexes 440', 450' of the sealing plates 422', 432' extends a majority of the height or thickness "T" of the jaw member 420', 430' and in embodiments, the maximum height "H2" of the sealing plate 422', 432' is almost the full height "T" of the jaw member 420', 430'.

The first and second legs 446a', 456a' and 446b', 456b' of each set 445', 455' have different lengths such that the apexes 440', 450' are off-center and disposed closer to the outer edges 422c', 432c' of the sealing plates 422', 432' than the central portions 422a', 432a' of the sealing plates 422', 432'. It is envisioned that the first and second legs 446a', 456a' and 446b', 456b' of each set 445', 455' may have the same length such that the apexes 440', 450' are centered in each of the side portions 422b', 432b' of the sealing plates 422', 432'. The first and second legs 446a', 456a' and 446b', 456b' may be linear or non-linear (e.g., curved). Energy provided to the jaw assembly 410' is transferred into the thickest part (e.g., the portions of the jaw members 420', 430' containing the apexes 440', 450') of the sealing plates 422', 432' (e.g., thermal energy is dissipated into the sealing plate 422', 432' cross-section and electrical energy rides the outer sealing plate surfaces) thereby minimizing thermal spread at the outer edges 422c', 432c' of the sealing plates 422', 432' and improving seal quality.

Figure 4D:
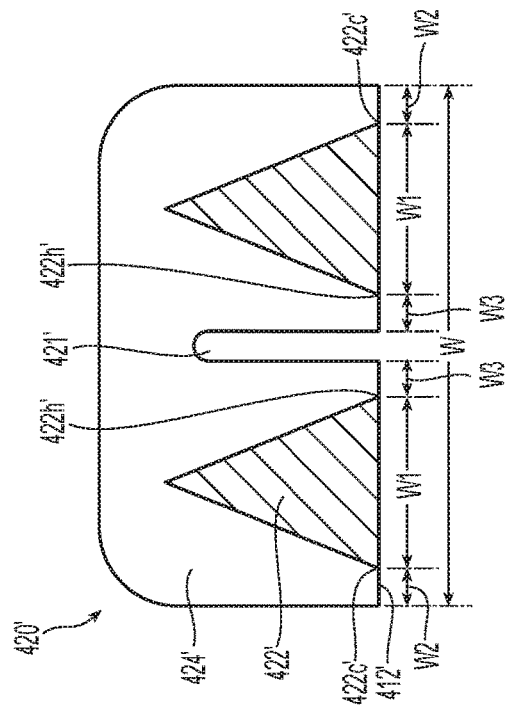
FIGS. 4C-4H are cross-sectional views of jaw members in accordance with embodiments of the disclosure.
Figure 4F:
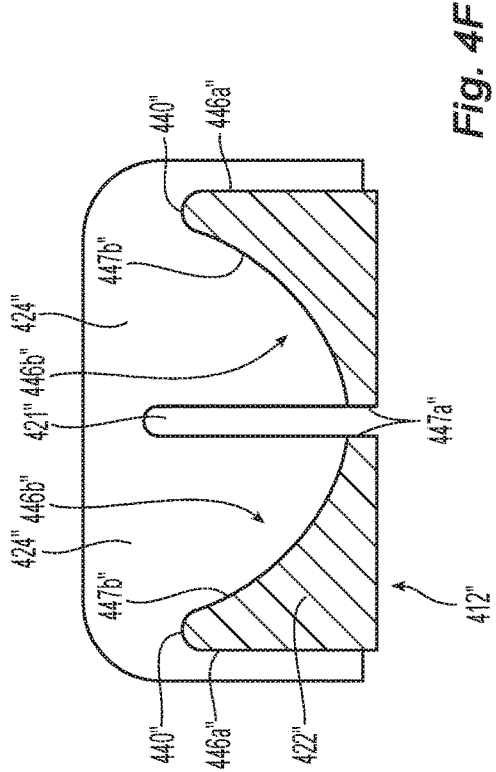
Figure 4C:
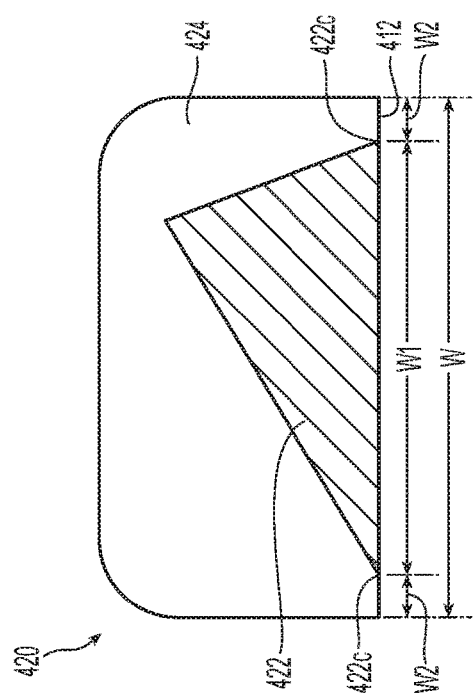

As shown in FIGS. 4C and 4D, the sealing plates 422, 422' may have a width "W1" extending through a portion (e.g., a majority) of the width "W" of the jaw members 420, 420'. The outer edges 422c, 422c' of the sealing plates 422, 422' may be spaced inwardly of the outer edges of the jaw members 420, 420' such that the insulators 424, 424' are disposed outwardly of the sealing plates 422, 422' around the outer periphery of the tissue contacting surface 412, 412' of the jaw member 420, 420' at a width "W2." As seen in FIG. 4D, the sealing plate 422' may include inner edges 422h' spaced outwardly of the knife slot 421' such that the insulator 424' is disposed between to the knife slot 421' and the sealing plate 422' at a width "W3." The width "W2," "W3" may be the same or different.

Figure 4E:
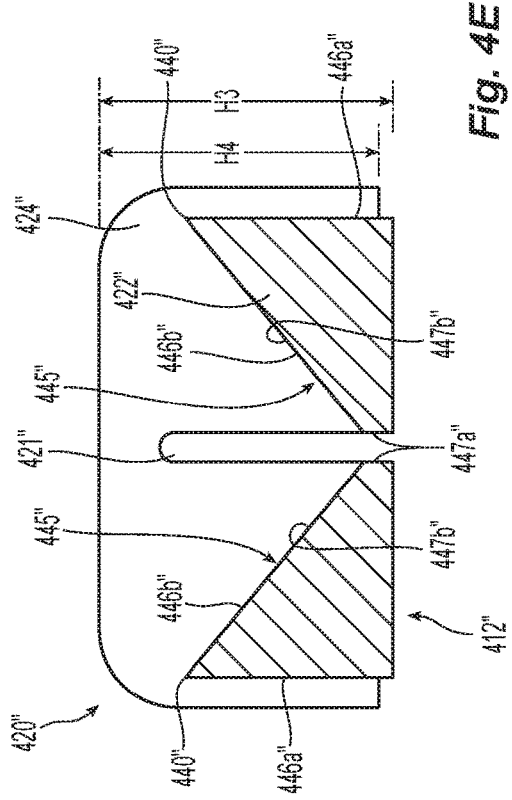

FIGS. 4E-4H show that the tissue contacting surface of the jaw members may be nonplanar. The sealing plate may extend outwardly beyond the insulator and the insulative support base of the jaw member. As seen in FIG. 4E, for example, the sealing plate 422" may extend downwardly towards the opposing jaw member (not explicitly shown) in stepped relation relative to the insulator 424" such that a height "H3" of the jaw member 420" including the sealing plate 422" is more than a height "H4" of the jaw member 420" that does not include the sealing plate 422".

Figure 4H:
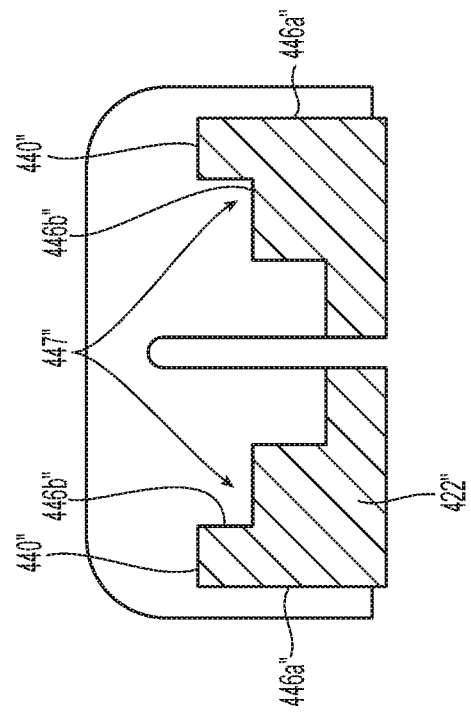
Figure 4G:
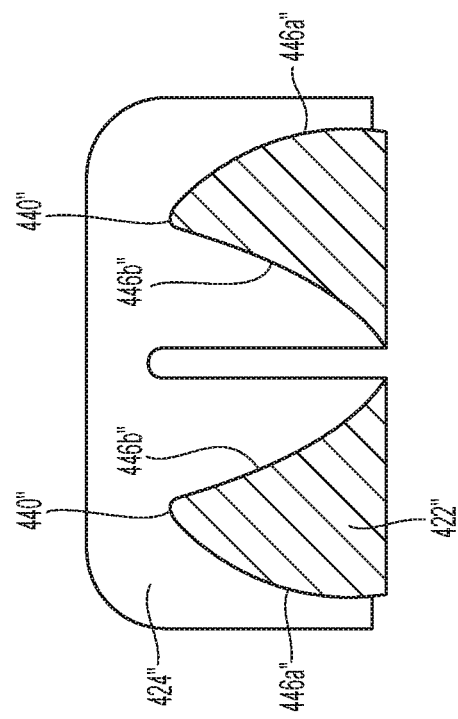

Further still, as seen in FIGS. 4E-4H, one or more legs of the sealing plates may be contoured to achieve the desired geometry and thus, thermal effect. As seen in FIG. 4E, the first leg 446a" of each of the two sets 445" of legs 446a", 446b" may extend linearly upwardly into the insulator 424" and the second leg 446b" may include a first segment 447a" extending linearly upwardly into the jaw member 420" adjacent to the knife slot 421" and a second segment 447b" angled towards the apex 440" of the sealing plate 422". As seen in FIG. 4F, the first leg 446a" of the sealing plate 422" may extend linearly upwardly to a rounded apex 440" and the second leg 446b" may include a linear first segment 447a" and a contour second segment 447b". The contoured second segment 447b" may be concave, convex, or have other non-linear configurations. As seen in FIG. 4G, the first leg 446a" of the sealing plate 422" may be convex and the second leg 446b" may be concave from the apex 440" towards the sealing surface 423". As seen in FIG. 4H, the first leg 446a" of the sealing plate 422" may extend linearly upwardly and the second leg 446b" may include a plurality of stepped segments 447" leading from the sealing surface 423" to a substantially flat apex 440". Other geometries are envisioned.

Figure 5:
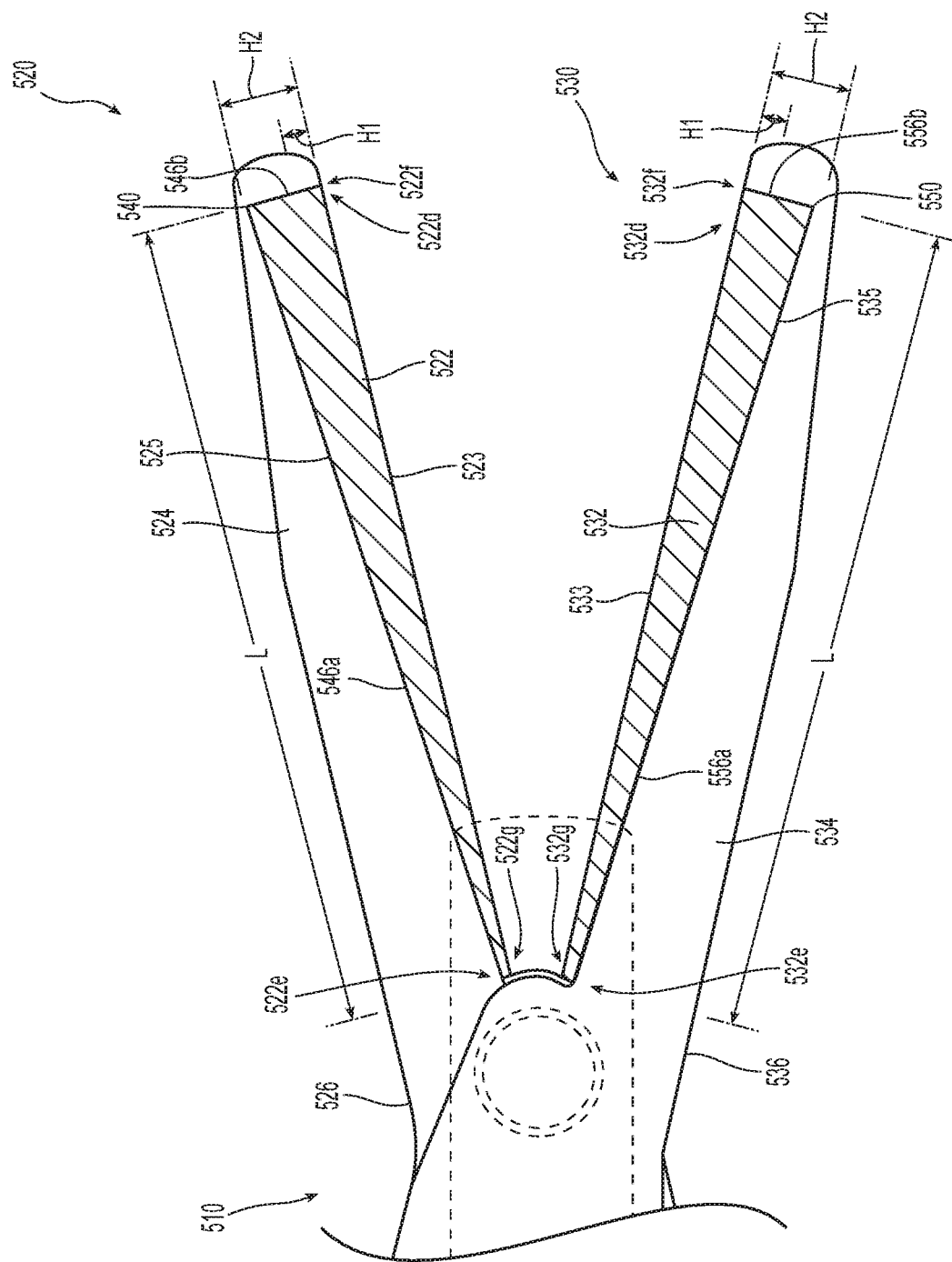
FIG. 5 is a side, cross-sectional view of jaw members in accordance with another embodiment of the disclosure.

FIG. 5 illustrates opposing jaws members 520, 530 of a jaw assembly 510. The jaw members 520, 530 include: electrically conductive sealing plates or substrates 522, 532; insulators 524, 534; and insulative support bases 526, 536. A vertical height or thickness of each of the sealing plates 522, 532 varies from a minimal height "H1" to a maximum height "H2" across the length "L" of the sealing plate 522, 532 and is consistent or uniform along the width "W" (FIG. 3B) thereof. The sealing plates 522, 532 include inwardly facing or sealing surfaces 523, 533 and outwardly facing surfaces 525, 535 that taper to apexes 540, 550 disposed about distal or tip portions 522d, 532d of the sealing plates 522, 532 such that the thickness of the sealing plate 522, 532 is greatest about the tip portions 522d, 532d of the sealing plates 522, 532.

The outwardly facing surface 525, 535 includes legs 546a, 556a and 546b, 556b that extend respectively from proximal and distal ends 522e, 532e and 522f, 532f of the sealing plate 522, 532 and taper towards the apexes 540, 550 such that the thickness of the sealing plate 522, 532 varies from a minimal height "H1" at a proximal or heel portion 522g, 532g of the sealing plate 522, 532 to a maximum height "H2" at the tip portion 522d, 532d of the sealing plates 522, 532. The legs 546a, 556a and 546b, 556b have different lengths such that the apex 540, 550 is disposed in the tip portion 522d, 532d of the sealing plate 522, 532. The thickness of the sealing plate 522, 532 increases along a majority of the length "L" of the jaw member 520, 530 such that energy is biased towards the tip portion 522d. 532d which improves tip sealing and overcomes non-parallel closure configurations.

It should be understood that the geometry of the sealing plate and/or the geometry, type, and/or location of the insulator relative to the sealing plate may be tailored to reduce thermal spread. For example, the geometry of the sealing plate (e.g., the position of the apex or apexes) may be optimized to control thermal mass location and thermal conductivity to minimize thermal spread by transferring heat into the sealing plate or away from the outer edges of the sealing plate. As another example, the type of insulator utilized in the jaw member, the insulator location relative to the sealing surface of the sealing plate, and/or the sealing plate and insulator geometry near the outer edges of the sealing plate may be tailored to control the current densities at the outer edges of the sealing plate, e.g., minimizing thermal spread at the outer edges of the sealing plate and thus, minimizing edge cutting.

With reference now to FIG. 6A, a top view of a sealing plate 622 of a jaw member 620 is shown. For the purposes, herein, one sealing plate 620 is described, however, both sealing plates of the jaw assemblies of the disclosure may be of the same or similar construction. The sealing plate 622 includes a longitudinally extending length "L" and a transversely extending width "W". The sealing plate 622 may have a generally flat or planar configuration, or may have a non-planar geometry such as those described above.

The sealing plate 622 includes a plurality of impedance zones 660 defined along the length "L" thereof. The impedance zones 660 are disposed adjacent each other along the entire length "L" of the sealing plate 622 from a proximal end 622e to a distal end 622f of the sealing plate 622, with each of the impedance zones 660 extending the entire width "W" of the sealing plate 622. The impedance zones 660 are formed by coating the sealing plate 622 with the same or different conductive, semiconductive, and/or insulative materials (e.g., conductors, such as stainless steel, semiconductors, such as silicon dioxide, or insulators) of the same or different thicknesses to achieve the desired thermal effect in each of the impedance zones 660. The impedance zones 660 may be formed in any manner within the purview of those skilled in the art, such as sputter coating.

The impedance zones 660 include a first or proximal zone 660a, a second or intermediate zone 660b, and a third or distal zone 660c. The first zone 660a is a high impedance zone. In embodiments, the electrical impedance of the first zone 660a is about or greater than 200 ohms (e.g., about 300 ohms) thereby having nearly zero tissue effect. The second zone 660b is a medium impedance zone having an electrical impedance less than that of the first zone 660a. In embodiments, the electrical impedance of the second zone 660b is about 100 ohms to achieve some tissue sealing effect. The third zone 660c is a low impedance zone having an electrical impedance less than the second zone 660b. In embodiments, the electrical impedance of the third zone 660c is about 0 ohms to about 20 ohms, and in some embodiment, about 10 ohms, to achieve a tissue sealing effect. Energy provided to the jaw member 620 is biased towards the tip portion 622d of the sealing plate 622 to improve tip sealing.

Each impedance zone 660 is homogenous in that the impedance value is consistent throughout the impedance zone 660. The impedance zones 660 are delineated by an interphase 662 between each adjacent impedance zone 660. The interphase 662 is a gradual transition or gradient transition from one impedance zone 660 to another. For example, the first zone 660a may have an impedance value of 200 ohms, while the second zone 660b may have an impedance value of about 100 ohms. The interphase 662 separating the first and second zones 660a, 660b may include an impedance value that gradually transitions from the first zone 660a to the second zone 660b. In other words, the portion of the interphase 662 closer to the first zone 660a has a higher impedance value (closer to 200 ohms) while the portion of the interphase 662 closer to the second zone 660b has a lower impedance value (closer to 100 ohms).

Alternatively, the impedance zones 660 may be separated by an interface. The interface is sharp transition at a common boundary between adjacent impedance zones 660. It should be understood that other embodiments in accordance with the disclosure may include one or more interphases, one or more interfaces, or combinations of interphases and interfaces between impedance zones.

The impedance zones 660 are shown as being substantially equal in area across the sealing surface 623 of the sealing plate 622. The impedance zones 660, however, may cover different amounts of area of the sealing surface 623 depending upon the desired thermal effect, as is within the purview of those skilled in the art. Further, while three impedance zones 660 are shown, it should be understood that the number of impedance zones 660 of the sealing plate 622 may vary (e.g., the sealing plate may include two impedance zones or may include a multitude of impedance zones forming a smooth or continuous gradient transition across the entire sealing plate).

As shown in FIG. 6B, a sealing plate 622' of a jaw member 620' includes a plurality of impedance zones 660' extending along a length "L" of the sealing plate 622' from a proximal end 622e' to a distal end 622f' thereof. The impedance zones 660' are disposed adjacent to each other and extend the entire width "W" of the sealing plate 622'. The impedance zones 660' form a gradient transition across the length "L" of the sealing plate 622' that spans from an area of low resistance at the proximal end 622e' of the sealing plate 622' to an area of high resistance at the distal end 622f' of the sealing plate 622'.

The sealing plate 622' includes a first material 661a', such as a conductive material (e.g., a metal) with low resistance characteristics, such as copper or aluminum, and a second material 661b', such as a conductive material (e.g., a metal) with high resistance characteristics, such as stainless steel. The first material 661a' is positioned at a proximal portion 622g' of the sealing plate 622' over an insulator (not shown) and forms a wire connection "C" with an electrical jaw lead 602' that supplies energy to the jaw member 620'. The second material 661b' is positioned over a portion of the first material 661a' and extends distally therefrom across the sealing surface 623' to the distal end 662f' of the sealing plate 622'. The thickness of the second material 661b' varies to create the impedance zones 660'. The sealing surface 623' of the sealing plate 622' is substantially planar, with the thickness of the second material 661b' varying inwardly towards an insulator over which the sealing plate 662' is positioned (see e.g., FIG. 3B).

FIG. 7A shows a sealing surface 723 of a sealing plate 722 of a jaw member 720. The sealing plate 722 includes a plurality of impedance zones 760 extending radially outwardly from a knife slot 721 defined therein, or in embodiments devoid of a knife slot 721, from about a central portion 722a of the sealing plate 722. The impedance zones 760 are concentric with each other and extend the length "L" of the entire circumference of the sealing plate 722, although it is contemplated that at least one of the impedance zones 760 may extend along a portion or arc of the circumference. The impedance zones 760 are formed by coating the sealing plate 722 with the same or different conductive, semiconductive, and/or insulative materials (e.g., conductors, such as stainless steel, semiconductors, such as silicon dioxide, or insulators) of the same or different thicknesses to achieve the desired thermal effect in each of the impedance zones 760.

The impedance zones 760 include a first or inner zone 760a and a second or outer zone 760b. The first and second zones 760a, 760b are generally ring-shaped in cross-sectional area and extend the length "L" of the sealing plate 722. In general, the first zone 760a is at least partially or substantially inside the second zone 760b, and the knife slot 721 is inside the first zone 760a.

The first zone 760a is a low impedance zone, and the second zone 760b is a high impedance zone. In embodiments, the first zone 760a has an electrical impedance of about 0 ohms to about 10 ohms, and the second zone 760b has an electrical impedance of about 250 ohms. The first zone 760a is immediately adjacent to and extends radially outwardly from the knife slot 721, and the second zone 760b is adjacent to and extends radially outwardly from the first zone 760a to outer edges 722c of the sealing plate 722. The first and second zones 760a, 760b are homogenous, as described above with regard to sealing plate 622, and include an interphase 762 disposed between the first and second zones 760a, 760b. Energy provided to the jaw member 720 is concentrated in the middle of the sealing plate 722 (about the first zone 760a), and the high impedance value of the second zone 760b reduces or eliminates thermal spread to surrounding tissue.

As shown in FIG. 7B, a sealing plate 722' of a jaw member 720' includes a plurality of impedance zones 760' defined concentrically therein. The impedance zones 760' extend the length "L" and the width "W" of the sealing plate 722'. The impedance zones 760' form a gradient transition outwardly from a central portion 722a' of the sealing plate 722' to the outer edges 722c' that spans from an area of low resistance about the central portion 722a' to an area of high resistance at the outer edges 722c'.

The sealing plate 722' includes a first material 761a', such as a conductive material (e.g., a metal) with low resistance characteristics, such as copper or aluminum, and a second material 761b', such as a conductive material (e.g., a metal) with high resistance characteristics, such as stainless steel. The first material 661a' forms a wire connection "C" with an electrical jaw lead 702' that supplies energy to the jaw member 720' at a proximal end 722e' of the sealing plate 722' and extends distally through the central portion 722a' of the sealing plate 722' adjacent to the distal end 722f' of the sealing plate 722'. The second material 761b' is disposed over the first material 761a' and extends along and across the sealing surface 723'. The thickness of the second material 761b' varies to create the impedance zones 760' of the jaw member 720'.

Turning now to FIGS. 8-8C, sealing plates may include a plurality of impedance regions each having one or more impedance zones. As seen in FIG. 8A, a sealing plate 822 of a jaw member 820 includes a plurality of impedance regions 870 extending along a length "L" of the sealing plate 822 from a proximal end 822e to a distal end 822f thereof. The impedance regions 870 are disposed adjacent to each other and extend the entire width "W" of the sealing plate 822. The impedance regions 870 includes a first impedance region 870a and a second impedance region 870b.

The first impedance region 870a extends from the proximal end 822e of the sealing plate 822 towards the distal end 822f adjacent to and proximal of the tip portion 822d. The first impedance region 870a includes a plurality of impedance zones 860 that forms a continuous gradient transition across the first impedance region 870a from a proximal impedance zone 860a that is a low impedance zone to a distal impedance zone 860b that is a high impedance zone. The second impedance region 870b is disposed at the tip portion 822d and has a single impedance zone 860c that may have an impedance value that is higher or lower than the distal impedance zone 860b of the first impedance region 870a depending upon the desired thermal effect. It should be understood that the plurality of impedance zones 860 in the first impedance region 870a may span, proximally to distally, from an area of high impedance to an area of low impedance and/or the second impedance region 870b may include more than one impedance zone 860.

As should in FIG. 8B, a sealing plate 822' includes a plurality of impedance regions 870' extending along a length "L" (FIG. 8A) of the sealing plate 822' from a proximal end 822e' to a distal end 822f' thereof. The impedance regions 870' are disposed adjacent to each other and extend the entire width "W" (FIG. 8A) of the sealing plate 822'. The impedance regions 870' includes a first impedance region 870a', a second impedance region 870b', and a third impedance region 870c'.

The first impedance region 870a' extends from the proximal end 822e' of the sealing plate 822' to about a central portion 822a' of the sealing plate 822'. The first impedance region 870a' includes a plurality of impedance zones 860' that forms a continuous gradient transition across the first impedance region 870a' from a proximal impedance zone 860a' that is a low impedance zone to a distal impedance zone 860b' that is a high impedance zone. The second impedance region 870b' is disposed about the central portion 822a' of the sealing plate 822' and has a single impedance zone 860c' that may have an impedance value that is higher or lower than the distal impedance zone 860b' of the first impedance region 870a'. The third impedance region 870c' extends from the central portion 822a' of the sealing plate 822' to the distal end 822f. The third impedance region 870c' includes a plurality of impedance zones 860' that forms a continuous gradient transition across the third impedance region 870c' from a proximal impedance zone 860d' that is a low impedance zone to a distal impedance zone 860e' that is a high impedance zone. It should be understood that the combinations and/or number of impedance zones 860' within each impedance region 870' may vary (e.g., increase or decrease proximally to distally).

Turning now to FIG. 8C, a sealing plate 822" includes a plurality of impedance regions 870" defined concentrically therein. The impedance regions 870" includes a first impedance region 870a" and a second impedance region 870b". The first impedance region 870a" extend laterally outwardly from the knife slot 821", or in embodiments devoid of a knife slot 820", about the center portion 822a" of the sealing plate 822". The second impedance region 870b" extends around the first impedance region 870a along the length "L" and the width "W" (FIG. 8A) of the sealing plate 822".

The first impedance region 870a" includes a plurality of impedance zones 860" forming a gradient transition that increases from an area of low impedance adjacent to the knife slot 821" outwardly towards an area of high impedance in the direction of arrow "A." The second impedance region 870b" includes a plurality of impedance regions 860" that increase from an area of low impedance at the proximal end 822e" of the sealing plate 822" to an area of high impedance at the distal end 822f' of the sealing plate 822" in the direction of arrow "B." While the first impedance region 870a" is shown longitudinally offset relative to each other on opposed sides of the knife slot 821", it should be understood that the first impedance region 870a" may be symmetrical.

Further, it should be understood that instead of a gradual transition, the impedance zones 860" within each of the impedance regions 870" may be separated by an interface or interphase and/or may increase or decrease proximally to distally and/or laterally.

It should be understood that the values, range of values of the impedance zones, and/or the configuration of the impedance zones on the sealing surface of the sealing plate depend on the specific energy application and desired tissue effect. For example, the impedance zones may be in pre-defined areas on the jaw member, such as along the tip portion or on one side of the sealing plate. As another example, the impedance zones may follow the jaw curvature or have a more complex contour. The impedance zones may be placed across from gap setting features.

While several embodiments of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the disclosure, and that such modifications and variation are also included within the scope of the disclosure. Therefore, the above description should not be construed as limiting, but merely as exemplifications of embodiments of the disclosure. Thus the scope of the embodiments should be determined by the appended claims and their legal equivalents, rather than by the examples given.

What is claimed is:

1. A jaw member comprising:
a support base;
an insulator supported within the support base; and
a sealing plate extending from a proximal end of the support base to a distal end of the support base, the sealing plate including a sealing surface configured to contact tissue and an outwardly facing surface opposite the sealing surface supported on the insulator, the sealing surface having at least two impedance zones, the at least two impedance zones having different impedance values and being contiguous and in electrical contact with one another at the sealing surface, wherein the sealing plate includes a first conductive material disposed at a proximal end of the sealing plate and a second conductive material positioned over at least a portion of the first conductive material and extending distally therefrom across the sealing surface to a distal end of the sealing plate.

2. The jaw member according to claim 1, where the at least two impedance zones are positioned longitudinally adjacent to each other.

3. The jaw member according to claim 1, wherein the at least two impedance zones are concentric with each other.

4. The jaw member according to claim 1, wherein the sealing plate includes a material having a different thickness in each of the at least two impedance zones.

5. The jaw member according to claim 1, wherein the first conductive material has a resistivity lower than that of the second conductive material.

6. The jaw member according to claim 1, wherein the sealing plate includes a first impedance region including the at least two impedance zones and a second impedance region including at least one impedance zone different than the at least two impedance zones of the first impedance region.

7. The jaw member according to claim 6, wherein the first impedance region extends from a proximal end of the sealing plate towards a distal end of the sealing plate adjacent to a tip portion, and the second impedance region is disposed at the tip portion of the sealing plate.

8. The jaw member according to claim 6, wherein the first impedance region extends from a proximal end of the sealing plate to a central portion of the sealing plate, the second impedance region is disposed about the central portion of the sealing plate, and a third impedance region extends from the central portion to a distal end of the sealing plate.

9. The jaw member according to claim 6, wherein the first impedance region is surrounded by the second impedance region.

10. The jaw member according to claim 1, wherein each of the at least two impedance zones has an impedance value greater than 0 ohms.

11. A jaw member comprising:
a sealing plate including a sealing surface having at least two impedance zones, the at least two impedance zones including a first zone having a first impedance value and a second zone having a second impedance value that is different from the first impedance value, the sealing surface including an interphase disposed between and contacting the first and second zones, the interphase having a variable impedance value that transitions from the first impedance value to the second impedance value, the at least two impedance zones and the interphase being electrically interconnected with each other across the sealing surface, and the first and second zones being concentric with each other; and
an insulator supporting the sealing plate thereon, the sealing plate extending from a proximal end of the insulator to a distal end of the insulator.

12. The jaw member according to claim 11, wherein each of the at least two impedance zones is homogeneous.

13. The jaw member according to claim 11, wherein the sealing plate further includes a third zone having a third impedance value that is different from the first and second impedance values.

14. The jaw member according to claim 11, wherein the first zone is disposed inside of the second zone, and the first impedance value is less than the second impedance value.

15. The jaw member according to claim 11, wherein the at least two impedance zones are substantially equal in area across the sealing surface of the sealing plate.

16. A jaw member, comprising:
a sealing plate including a sealing surface having at least two impedance zones, wherein the at least two impedance zones are coatings of conductive materials disposed on the sealing surface of the sealing plate, the at least two impedance zones including a first zone having a first impedance value and a second zone having a second impedance value that is different from the first impedance value, the sealing surface including an interphase disposed between and contacting the first and second zones, the interphase having a variable impedance value that transitions from the first impedance value to the second impedance value, the at least two impedance zones and the interphase being electrically interconnected with each other across the sealing surface; and
an insulator supporting the sealing plate thereon.

* * * * *